US008311641B2

(12) United States Patent
Zhu et al.

(10) Patent No.: US 8,311,641 B2
(45) Date of Patent: Nov. 13, 2012

(54) METHOD AND APPARATUS FOR GENERATING A LOCALIZED HEATING

(75) Inventors: Yudong Zhu, Scarsdale, NY (US); Thomas Kwok-Fah Foo, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 1011 days.

(21) Appl. No.: 12/328,444

(22) Filed: Dec. 4, 2008

(65) Prior Publication Data

US 2010/0145420 A1   Jun. 10, 2010

(51) Int. Cl.
*A61F 2/00* (2006.01)
(52) U.S. Cl. ...................................................... 607/103
(58) Field of Classification Search .................. 600/410; 324/316, 318; 607/103
See application file for complete search history.

(56) References Cited

U.S. PATENT DOCUMENTS

| 4,669,475 A | 6/1987 | Turner |
| 4,702,262 A | 10/1987 | Andersen et al. |
| 5,441,532 A | 8/1995 | Fenn |
| 5,540,737 A | 7/1996 | Fenn |
| 5,564,421 A * | 10/1996 | Ehnholm ............... 600/410 |
| 6,807,446 B2 | 10/2004 | Fenn et al. |
| 7,307,419 B2 | 12/2007 | Zhu et al. |
| 7,336,145 B1 | 2/2008 | Zelinski et al. |
| 2005/0134268 A1 | 6/2005 | Zhu |
| 2007/0247155 A1 | 10/2007 | Zhu |

FOREIGN PATENT DOCUMENTS

WO   WO0180949   11/2001

OTHER PUBLICATIONS

Kroeze et al., "Regional Hyperthermia Applicator Design using FDTD Modelling", Physics in Medicine and Biology, 46 (2001) 1919-1935.
Szasz, "Hyperthermia, a Modality in the Wings", Journal Cancer Res. Ther., (2007) vol. 3, Issue 1, pp. 1-21.
Fujita, "Effects of Blood Perfusion Rate on the Optimization of RF-Capacitive Hyperthermia", IEEE Transactions on Biomedical Engineering, vol. 45, No. 9, Sep. 1998, pp. 1182-1186.
Wiersma et al. "A Flexible Optimization Tool for Hyperthermia Treatments with RF Phased Array Systems", International Journal of Hyperthermia, vol. 18, Issue 2, Mar. 2002, pp. 1-2.

* cited by examiner

*Primary Examiner* — Manuel Mendez
(74) *Attorney, Agent, or Firm* — Marie-Claire B. Maple

(57) ABSTRACT

A method and apparatus for generating a localized heating are provided, the method comprising: transmitting a spatially localized or shaped electromagnetic field via a plurality of coils to a subject and generating magnetic resonance signals; performing magnetic resonance imaging based on the magnetic resonance signals to generate an image of a region of interest of the subject; and controlling the plurality of the same imaging coils to radiate radio frequency (rf) energy to generate the localized heating on a region of interest. The invention provide a more efficient manner for generating localized heating and means for verifying the heating pattern without the need to measure temperature rises in the patient. This is useful to check the localization prior to the application of hyperthermia.

19 Claims, 6 Drawing Sheets

METHOD AND APPARATUS FOR GENERATING A LOCALIZED HEATING

FIELD OF THE INVENTION

The subject matter disclosed herein relates generally to a method and an apparatus for generating a localized heating, and more particularly, to a method and an apparatus for generating a localized heating on a region of interest of a subject by a magnetic resonance imaging (MRI) system.

RELATED ART

In the field of oncology, hyperthermia is frequently used in conjunction with chemotherapy to improve an efficiency of tumor cell killing. Radio frequency (RF) hyperthermia is a standard tool in the oncology field to generate spatially controlled (localized) heating patterns within a body. Conventional RF hyperthermia uses an array of dipole antennas placed around the body and delivers the necessary energy via a continuous or pulsed RF waveform.

An amplitude and a phase of the RF waveform at each element is varied to provide the necessary spatial localization. Verification of the localized heating pattern is performed via invasive thermocouples that directly measure the temperature rise or non-invasively using MR or infrared thermometry. In addition, to improve the efficiency of delivering the RF energy to the patient, a water-filled bag surrounding the patient is used to increase the coupling of the RF to the body.

MR thermometry, using proton resonance frequency (PRF) shifts, has been used with RF hyperthermia to monitor the heating pattern and to adjust the application of RF energy so as to target only the region of interest (e.g., Kowalski M E, et al, IEEE Trans Biomed Eng 2002; 49: 1229-41). However, cumbersome water-filled bags are used and the heating pattern is adjusted and verified based on the image-based thermometry data. Therefore, an improved method and apparatus for generating a localized heating in a region of interest of a subject overcoming foregoing disadvantages is desired.

SUMMARY OF THE INVENTION

In a first aspect, a method for generating a localized heating is provided. The method includes the steps of: transmitting a spatially localized or shaped electromagnetic field via a plurality of coils to a subject and generating magnetic resonance signals; performing magnetic resonance imaging based on the magnetic resonance signals to generate an image of a region of interest of the subject; and controlling the plurality of the coils to radiate radio frequency (rf) energy to generate the localized heating in a region of interest.

In a second aspect, an apparatus for generating localized heating is provided. The apparatus includes: a plurality of coils configured to transmit a spatially localized or shaped electromagnetic field to a subject and to generate magnetic resonance signals; an imaging device configured to perform magnetic resonance imaging based on the magnetic resonance signals to generate an image of a region of interest of the subject; and a control device configured to control the plurality of the coils to radiate RF energy to generate the localized heating on the region of interest.

In a third aspect, a method for generating a localized heating is provided. The method includes: transmitting radio frequency energy via a plurality of coils to a subject; and generating unique radio frequency waveforms on each of the coils to generate an arbitrary specific absorption rate distribution in the subject to enable spatially localized heating.

In a fourth aspect, a method for generating a localized heating pattern and imaging is provided. The method and apparatus includes: a plurality of coils configured to transmit a spatially localized or shaped time-varying magnetic field to excite spins of interest within the body to generate magnetic resonance signals. Furthermore, the same configuration of coils is used to also transmit a spatially localized or shaped electric field to generate an arbitrary specific absorption rate distribution in the subject to enable spatial localized heating.

BRIEF DESCRIPTION OF THE DRAWINGS

The features and advantages of the invention will become apparent from the following detailed description of the embodiments of the invention when read with the accompanying drawings in which.

DETAILED DESCRIPTION

Figure 1:
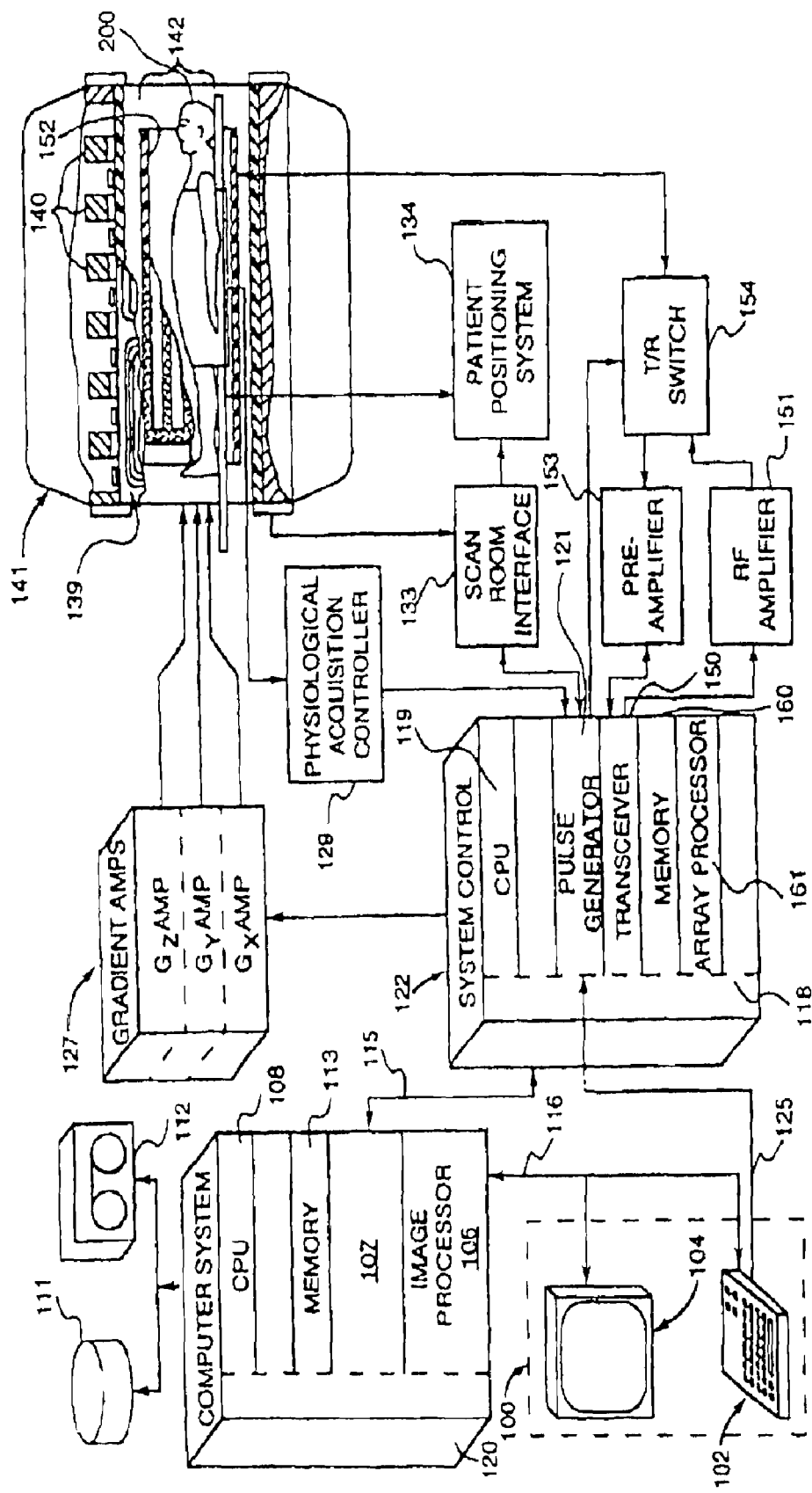
FIG. 1 illustrates a block diagram of a system for generating a localized heating in accordance with certain embodiments of the invention.

The embodiments of the invention will be described in detail with respect to the figures below. Taking into account that detailed description of some related art would confuse the invention, the detailed description thereof will not be provided herein. In the drawings, the same reference numerals are used to indicate the same elements or components performing the same functions.

FIG. 1 illustrates a block diagram of a system for generating the localized heating in accordance with embodiments of the invention. The system is an MR imaging system that incorporates the embodiments of the invention. The MRI system could be, for example, a GE-Signa MR scanner available from GE Medical Systems, Inc., which is adapted to perform the method of the invention, although other systems could be used as well.

The operation of the system is controlled from an operator console 100 which includes a keyboard and control panel 102 and a display 104. The console 100 communicates through a link 116 with a separate computer system 120 that enables an operator to control the production and display of images on the screen 104. The computer system 120 includes a number of modules which communicate with each other through a backplane. These modules include an image processor module 106, a CPU module 108, and a memory module 113, known in the art as a frame buffer for storing image data arrays. The computer system 120 is linked to disk storage 111 and tape drive 112 for storage of image data and programs, and it communicates with a separate system control 122 through a high speed serial link 115.

The system control 122 includes a set of modules connected together by a backplane. These modules include a CPU module 119 and a pulse generator module 121 which connects to the operator console 100 through a serial link 125. It is through this link 125 that the system control 122 receives commands from the operator which indicate operations that are to be performed. The pulse generator module 121 operates the system components to carry out the desired operations. It produces data that indicate the timing, strength, and shape of the radio frequency (RF) pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives subject data from a physiological acquisition controller 129 that receives signals from a number of different sensors connected to the subject 200, such as ECG signals from electrodes or respiratory signals from a bellows. And finally, the pulse generator module 121 connects to a scan room interface circuit 133 which receives signals from various sensors associated with the condition of the subject 200 and the magnet system. It is also through the scan room interface circuit 133 that a positioning device 134 receives commands to move the subject 200 to the desired position for the scan.

The gradient waveforms produced by the pulse generator module 121 are applied to a gradient amplifier system 127 comprised of $G_x$, $G_y$, and $G_z$ amplifiers. Each gradient amplifier excites a corresponding gradient coil in an assembly 139 generally designated to produce the magnetic field gradients used for position encoding acquired signals. The gradient coil assembly 139 forms a part of a magnet assembly 141 which includes a polarizing magnet 140 and a RF coil system 152. Volume 142 is shown as the area within magnet assembly 141 for receiving subject 200 and includes a patient bore. As used herein, the usable volume of a MRI scanner is defined generally as the volume within volume 142 that is a contiguous area inside the patient bore where homogeneity of main, gradient and RF fields are within known, acceptable ranges for imaging. A transceiver module 150 in the system control 122 produces pulses that are amplified by a RF amplifier system 151 and coupled to the RF coil system 152 by a transmit/receive switch system 154. The resulting signals radiated by the excited nuclei in the subject 200 can be sensed by the same RF coil system 152 and coupled through the transmit/receive switch system 154 to a preamplifier system 153. The amplified MR signals are demodulated, filtered, and digitized in the receiver section of the transceiver 150. The transmit/receive switch 154 is controlled by a signal from the pulse generator module 121 to electrically connect the RF amplifier system 151 to the coil system 152 during the transmit mode (i.e., during excitation) and to connect the preamplifier system 153 during the receive mode. The transmit/receive switch system 154 also enables a separate RF coil (not shown, for example, a head coil or surface coil) to be used in either the transmit mode or the receive mode.

In the embodiments of the invention, the RF coil system 152 is a transmit/receive coil array assembly that will be described with reference to FIGS. 2-3. During the transmit mode, the RF pulse waveforms produced by the pulse generator module 121 are applied to a RF amplifier system 151 comprised of multiple amplifiers. Each amplifier controls the current in a corresponding component coil of the coil system 152 in accordance with the amplifier's input RF pulse waveform. With the transmit/receive switch system 154, the RF coil system 152 is configured to perform transmission and reception simultaneously or alternatively.

As used herein "adapted to", "configured" and the like refer to mechanical or structural connections between elements to allow the elements to cooperate to provide a described effect; these terms also refer to operation capabilities of electrical elements such as analog or digital computers or application specific devices such as an application specific integrated circuit (ASIC) that is programmed to perform a sequence to provide an output in response to given input signals.

The MR signals picked up by the RF coil system 152 or a separate receive coil are digitized by the transceiver module 150 and transferred to a memory module 160 in the system control 122. When the scan is completed and an entire array of data has been acquired in the memory module 160, an array processor 161 operates to Fourier transform the data into an array of image data. These image data are conveyed through the serial link 115 to the computer system 120 where they are stored in the disk memory 111. In response to commands received from the operator console 100, these image data may be processed by the image processor 106 and conveyed to the operator console 100 and presented on the display 104, or they may be further archived on the tape drive 112. Further processing is performed by the image processor 106 that includes reconstructing acquired MR image data.

Figure 2:
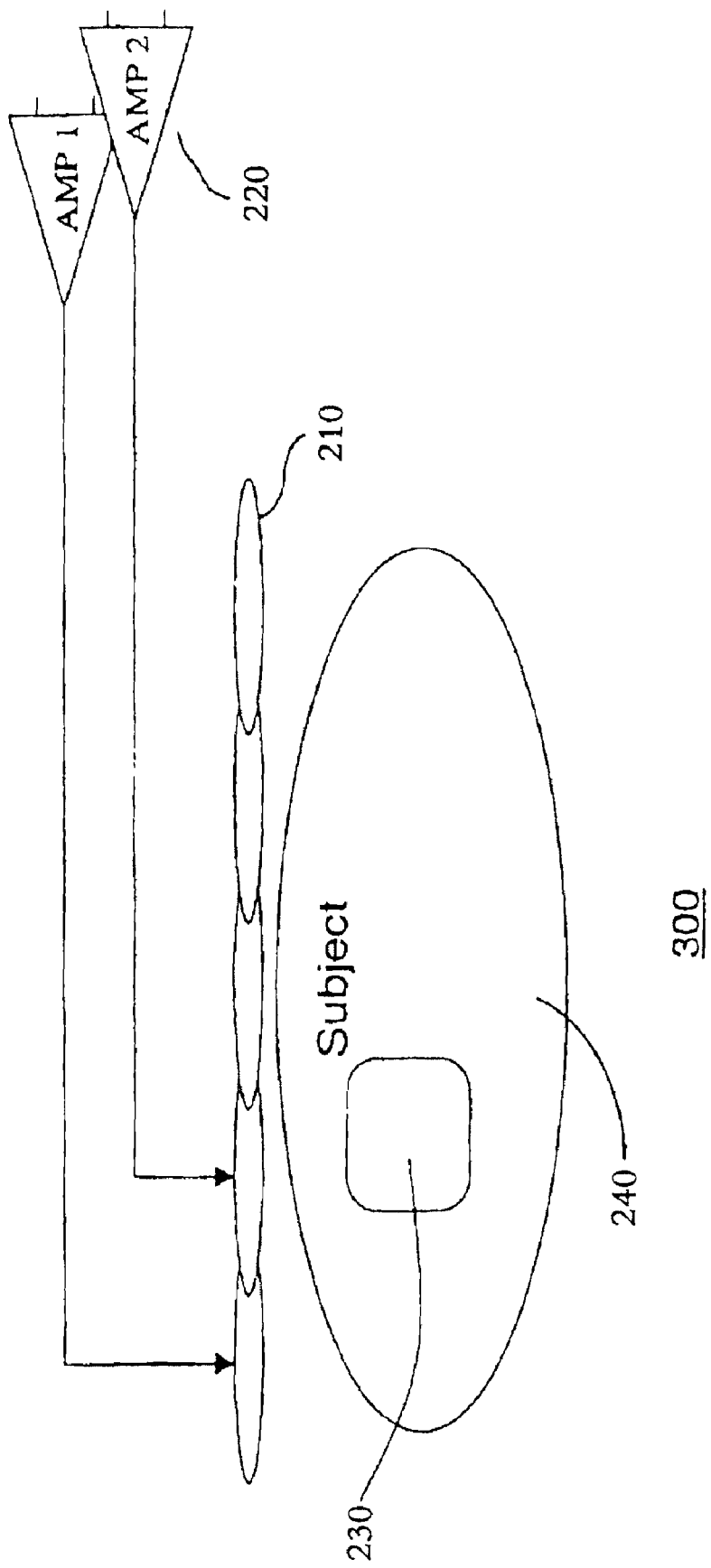
FIG. 2 is a simplified block diagram showing a linear coil array in accordance with one embodiment of the invention.

Referring to FIG. 2, in one embodiment, a transmit/receive coil array assembly 300 for use in the embodiment of the invention comprises a plurality of radio frequency (rf) coils 210 configured for transmitting in parallel during transmission mode and a plurality of RF amplifiers 220 coupled to the corresponding RF coils adapted to generate a controlled current in each of the RF coils, and wherein the controlled current being used for defining and steering a region of interest 230 of the subject 200 within the system. In FIG. 2, the placement of the coils is substantially linear.

Figure 3:
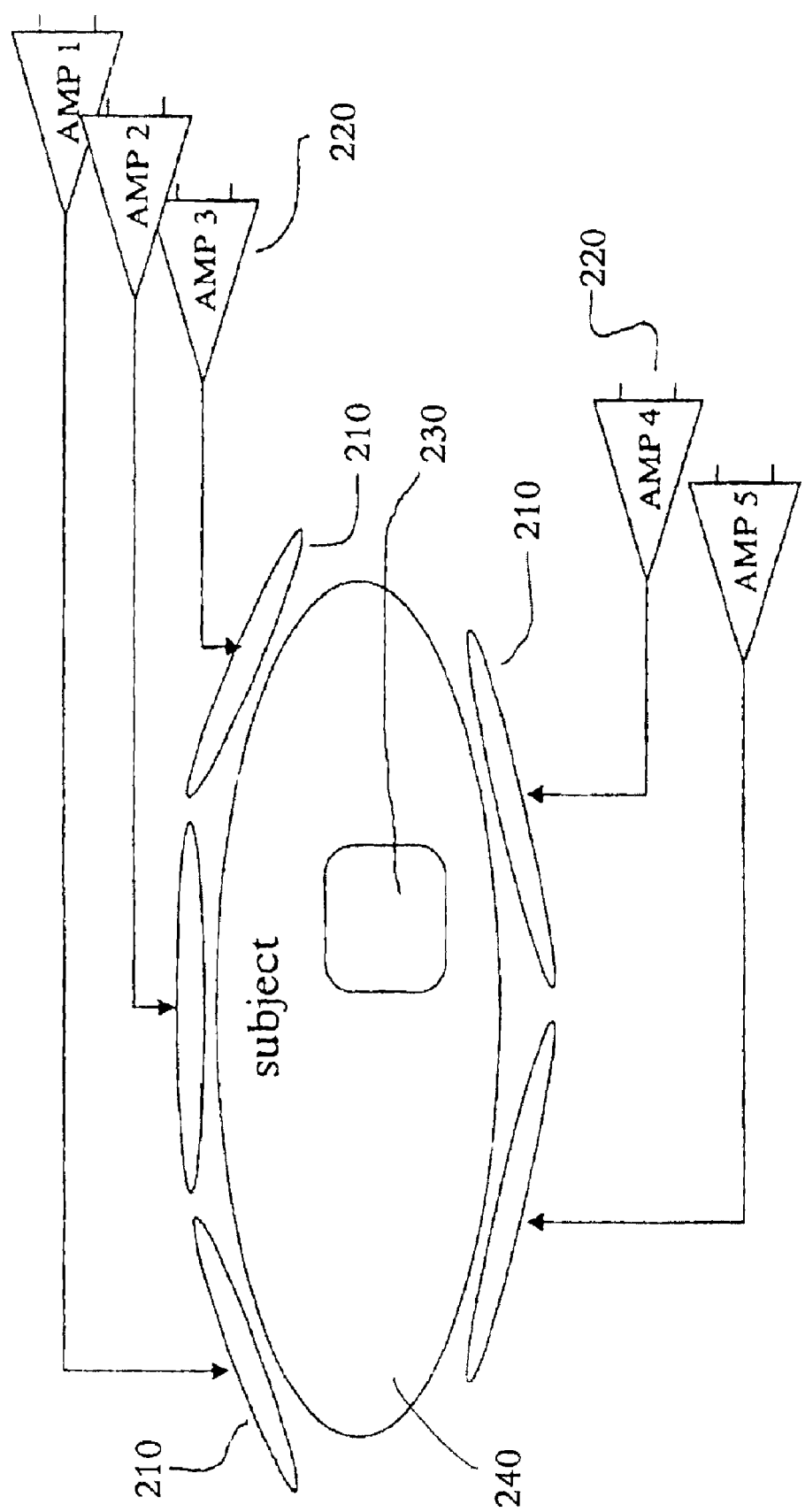
FIG. 3 is a simplified block diagram showing a coil array in accordance with another embodiment of the invention.

Referring to FIG. 3, an alternative embodiment is shown, in which RF coils 210 are arranged in an equally distributed pattern about the subject 200, such as a circle.

Hereinafter, the embodiments of the invention will be further described in details in conjunction with the drawings.

Figure 4:
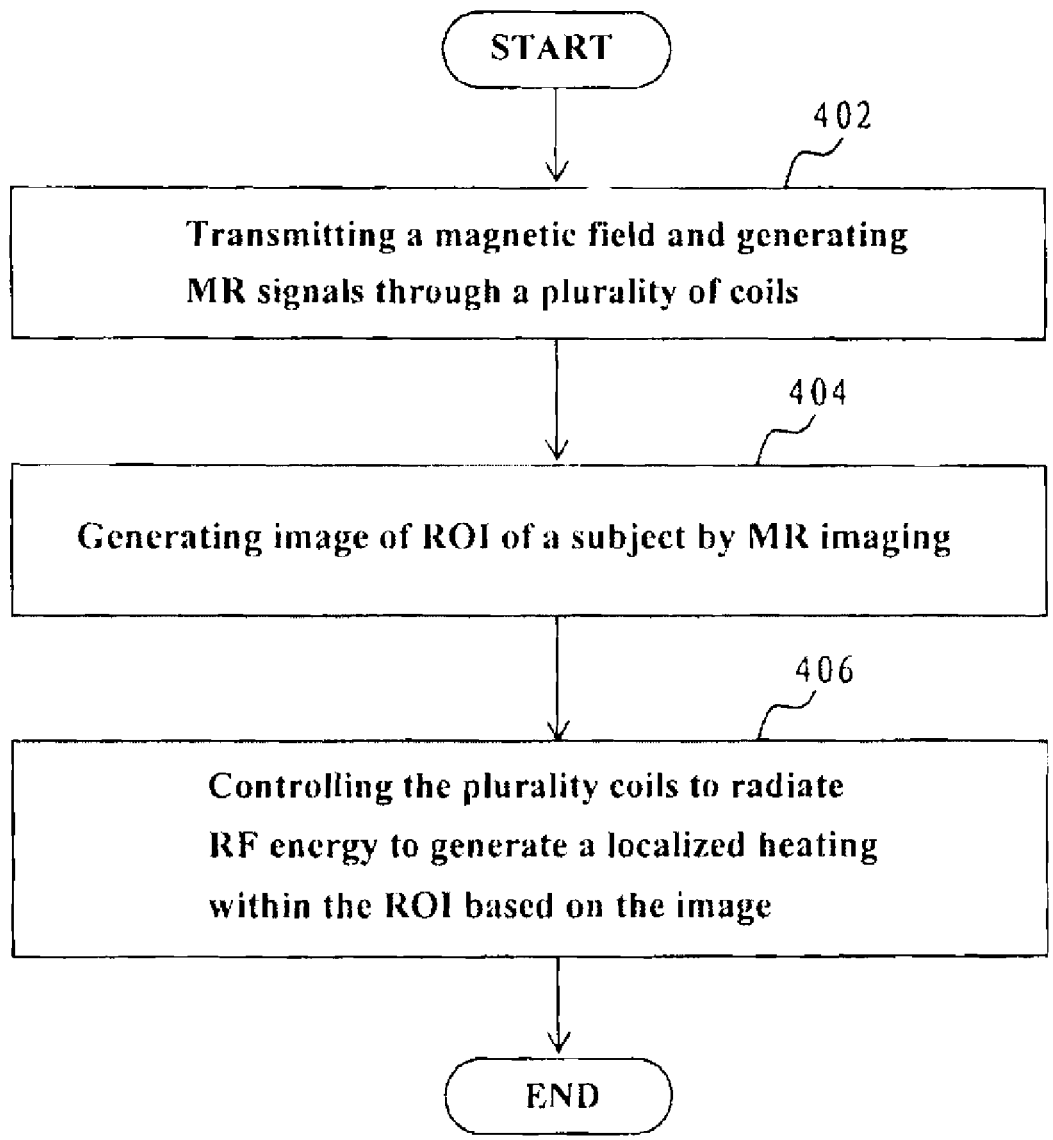
FIG. 4 is a flow chart showing operation of an apparatus in accordance with one embodiment of the invention.

FIG. 4 is a flow chart showing the operations of the apparatus in accordance with one embodiment of the invention.

As shown in FIG. 4, the apparatus of the embodiment of the invention is used to generate the localized heating based on the magnetic resonance imaging (MRI). After the operation is started, in Step 402, a spatially localized or shaped electromagnetic field is transmitted to the subject 200 and magnetic resonance (MR) signals are generated through a plurality of coils. Specifically, the pulse generator module 121 produces the RF pulse waveforms, and applies the RF pulse waveforms to the RF amplifier system 151 comprised of multiple amplifiers which control the current in each component coil of the coil system 152, which comprises a plurality of coils 210 as shown in FIGS. 2 and 3, in accordance with the amplifier's input RF pulse waveform, so that the coil system 152 transmits the electromagnetic field to the subject 200 and generates MR signals.

Then, in Step 404, the MR imaging is performed based on the MR signals to generate image of a region of interest 230 of the subject 200. Specifically, the coil system 152 picks up the MR signals. With the transmit/receive switch system 154, the MR signals picked up by the coil system 152 are digitized by the transceiver module 150 and transferred to a memory module 160 of the system control 122.

When an entire array of data has been acquired in the memory module 160, an array processor 161 operates to Fourier transform the data into an array of image data. These image data are conveyed through the serial link 115 to the computer system 120 where they are stored in the disk memory 111. In response to commands received from the operator console 100, or automatically, these image data are further processed by the image processor 106 and conveyed to the operator console 100 and presented on the display 104. In addition, these image data may also be archived on the tape drive 112. Here, the image processor 106 performs MR imaging based on the MR signals to generate image of the region of interest 230 of the subject 200.

Then, in Step 406, the plurality of coils 210 are controlled to radiate radio frequency energy via a RF waveform to generate localized heating in the region of interest 230. Specifically, the pulse generator 121 and the coil system 152 are controlled by the CPU module 108 and/or the CPU module 119 to radiate radio frequency energy via the RF pulse waveform to generate localized heating within a range of the region of interest 230 based on the image of the region of interest 230.

Implicit in the preceding description of the work flow is the incorporation of a calibration step wherein the $B_1$ field distribution for each of the coil elements 210 in the multiple element coil array is measured. This information is used to compute the radio frequency amplitudes and phase for each coil element in order to generate the appropriate distribution of the electric field in the subject 240, and consequently, the heating or specific absorption rate distribution in the subject 240.

In one embodiment, a localized heating is generated by the apparatus of the embodiment of the invention based on the electromagnetic field. Specifically, a set of weights (radio frequency coil amplitude and phase for each coil element 210) are calculated by CPU 108 or 119 such that the magnitude of the magnetic field equals that of a desired magnetic field within the region of interest 230. A magnetic field excitation pattern that can be observed in the image is generated by means of the radio frequency energy based on the set of weights. The corresponding radio frequency electric field distribution is inferred by comparing the radio frequency magnetic field excitation pattern in the image. Then, the spatially localized heating pattern is predicted by the inferred radio frequency electric field distribution. The localized heating pattern can also be generated by using unique radio frequency (rf) waveforms in each of the plurality of coils 210 and/or simultaneously adjusting the amplitude and phase of the unique radio frequency waveforms. In either case, the individual coil element weights (amplitude and phase) that results in a desired localized heating pattern or distribution will also yield a unique magnetic ($B_1$) field excitation pattern that can be visualized in a magnetic resonance image. The heating pattern (electric field distribution) then corresponds to the MR $B_1$-field excitation pattern. In one embodiment, the unique radio frequency waveform is a unit radio frequency sinusoidal pulse. The use of other waveforms will also yield similar results.

In other words, a set of weights (amplitude and phase of each coil element 210) are calculated by CPU 108 or 119 such that the magnitude of the magnetic field equals that of a desired magnetic field within the region of interest 230, an electric field is generated by the plurality of coils based on the same set of weights, and the localized heating is generated by the apparatus based on the applied electromagnetic field with the same set of computed weights.

Specifically, the above procedure will be further described in detail as below.

The embodiment of the invention is based on the parallel transmit technique that was originally intended to provide a more homogeneous transmit $B_1$-field ($B_1+$) and also to reduce the overall SAR. Note that $$SAR = \frac{1}{2}\sigma|E|^2 \tag{1}$$

wherein $\sigma$ is the tissue conductivity and $|E|^2$ denotes the magnitude squared of the associated E-field, where $|E|^2=\sqrt{(E_x^2+E_y^2+E_z^2)}$.

The CPU module 108 calculates a set of weights such that the magnitude-squared difference between the generated magnetic field and a desired magnetic field, which is determined based on the image, is minimized within the region of interest 230. For example, for an array of N coils (N denotes number of coils, m is coil index, and n is the index for spatial location), in parallel transmit, the resulting magnetic field is given as the weighted sum of the individual transmit coils' magnetic fields $$b_n = \sum_{m=1}^{\#coils} B_{n,m} * w_m \tag{2}$$

wherein $B_{n,m}$ is the magnetic field generated at location n by coil m when the coil alone is driven by a unit radiofrequency sinusoidal pulse. $w_m$, a complex scalar capturing the amplitude and phase control of a radio frequency sinusoidal pulse that drives the mth coil, effectively represents the weight for the mth coil in generating the net magnetic field at discrete points n.

With the array of N coils, the method of the embodiment of the invention for generating localized heating patterns relies on the application of unique RF waveforms, such as a unit radio frequency sinusoidal pulse, to each individual coil. This is in contrast to the conventional RF hyperthermia techniques that only modulate the amplitude and phase of the same waveform to each coil. Our invention allows the modulation of amplitude and phase of waveforms to each coil without restricting the same waveform to all coil elements.

For a parallel transmit approach seeking to generate as homogeneous a $B_1+$ field as possible, the set of weights $\{w_m\}$ can be calculated such that the magnitude squared difference between the $b_n$ and the desired $b_n'$ field, which is determined based on the image of a given region-of-interest (ROI) 230 of the subject 200 by experiment, as small as possible within the ROI. That is to calculate the set of weights such that the least-squared difference is as small as possible, i.e.,:

$$|b_n'-b_n|^2 \to 0 \tag{3}$$

wherein $b_n$ is the magnetic field generated by the multiple coils array defined in Equation (2), while $b_n'$ is the desired magnetic field distribution.

Then, a magnetic field excitation pattern that can be observed in the image is generated by the computer system 120 by means of the radio frequency energy based on the set of weights.

Then, the corresponding radio frequency electric field distribution is inferred by comparing the radio frequency magnetic field excitation pattern in the image. Specifically, the CPU module 108 calculates an electric field distribution generated by the coil system 152 based on the same set of calculated weights such that the electric field is maximum in the region of interest 230 and minimum outside the region of interest 230.

The net electric field that is produced by the multiple transmit coils can be written as $$e_n = \sum_{m=1}^{\#coils} E_{n,m} * w_m \quad (4)$$

wherein $E_{n,m}$ is the electric field generated at location n by coil m when the coil alone is driven by the unit radiofrequency sinusoidal pulse. Based on equation (4), the set of weights may also be calculated such that the magnitude of the electric field equals that of a desired electric field within the region of interest.

According to the above equation (4) and based on the set of weights $\{w_m\}$ which is previously calculated, the electric field distribution that is produced in the meanwhile by the multiple transmit coils can be obtained.

In order to modify the SAR distribution, we can compute the new cost function to maximize the SAR in the given ROI 230 while minimizing the SAR in other areas (outside the ROI 230). The cost function can then be $$|e_n'|^2 - |e_n|^2 \rightarrow 0 \quad (5)$$

wherein $e_n$ is the net electric field generated by the multiple transmit array, while $e_n'$ is the desired electric field distribution. Note that over the given ROI, $|e_n'|^2$ is maximum, and in other areas, $|e_n'|^2$ is minimum.

In addition, the electric field distribution may also be predicted by means of the magnetic field based on the following Maxwell's equations:

$$\vec{E} = (\mu(\sigma - j\omega \in))^{-1} \nabla \times \vec{B} \quad (6)$$

where $\mu$ is the magnetic permeability, $\sigma$ is the conductivity, and $\delta$ is the dielectric constant (permittivity), with $\omega$ as the resonant frequency, and $j = (-1)^{1/2}$. $B_1$ field calibration or mapping procedure can be performed to determine the $B_{n,m}$ fields, i.e. $\vec{B}$, for each transmit coil. Then, from the equation (6), $E_{n,m}$ can be approximated together with using representative values for the tissue constants and the value of the $\vec{B}$.

Then, the spatially localized heating pattern is predicted by the computer system 120 by means of the inferred radio frequency electric field distribution by the measured radio frequency magnetic field excitation pattern in the image.

Further, the electric field distribution can be predicted from the magnetic field excitation pattern in the image using an approximation of the z-component of the magnetic ($B_1$) field. The approximation of the z-component of the magnetic ($B_1$) field is constrained to a subset of allowable solutions by the boundary values set by the imaging experiment.

Finally, the CPU module 108 controls the pulse generator 121 and the coil system 152 (the plurality of coils 210) to generate the localized heating by generating unique radio frequency (rf) waveforms in each of the plurality of coils 210 or adjusting the amplitude and phase of the unique radio frequency waveforms based on the predicted spatially localized heating pattern and/or the calculated electric field distribution. In the embodiment, the unique radio frequency waveform is a unit radio frequency sinusoidal pulse, but any other waveform can also be used.

As stated above, in order to localize the heating pattern within the ROI, it could be verified that the $B_1+$ field generated is as expected. The verification can be performed based on equation (2) by using an imaging experiment and matching the expected $B_1+$ field pattern with the result of the experiment. This can be performed while keeping the power levels sufficiently below that needed to cause heating or temperature rises. Note that in this configuration, the same coil array is used both for MR imaging and also for generating the localized heating pattern. In addition, the large water-filled coupling bags are no longer necessary.

In one embodiment, the MR imaging and the localized heating is performed simultaneously. Specifically, with the transmit/receive switch 154, the transceiver module 150 radiates RF energy via the RF waveform and receives MR signals simultaneously. In another embodiment, the MR imaging and the localized heating is performed in an interleaved fashion. Specifically, with the transmit/receive switch 154, the transceiver module 150 radiates RF energy via the RF waveform and receives MR signals alternatively. The localized heating and MR imaging can also be interleaved by first applying a series of weights and waveforms that optimizes localized heating in a region of interest, and then applying a different series of weights and waveforms that optimizes imaging in the same region of interest.

The specific structure of the apparatus of the embodiment as shown in FIG. 1 does not set a limitation to the scope of the invention. For example, FIG. 5 illustrates a simplified block diagram of an apparatus for generating a localized heating in accordance with another embodiment of the invention.

Figure 5:
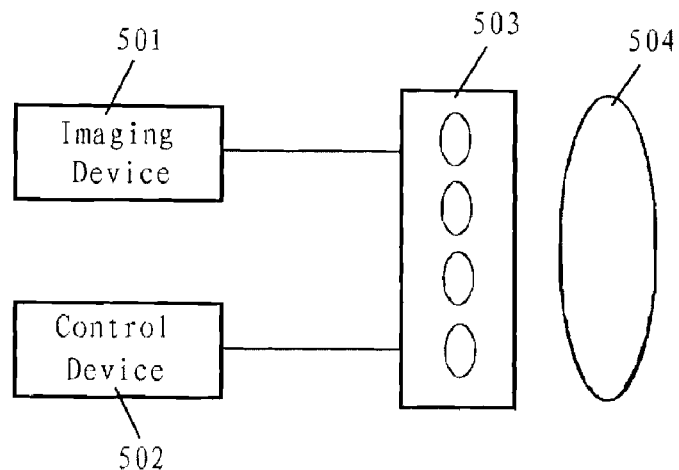
FIG. 5 illustrates a simplified block diagram of the apparatus for generating a localized heating in accordance with another embodiment of the invention.

As shown in FIG. 5, the apparatus of the embodiment of the invention for generating a localized heating may comprises a plurality of coils 503 configured to transmit a spatially localized or shaped electromagnetic field to the subject 504 and to generate MR signals, an imaging device 501 configured to perform MR imaging based on the MR signals to generate an image of a region of interest of the subject 504, and a control device 502 configured to control the plurality of coils 503 to radiate radio frequency energy via a RF pulse waveform to generate the localized heating in the region of interest 230 based on the image.

In one embodiment, the control device 502 generates unique radio frequency waveforms for each of said coils or adjusts the amplitude and phase of the unique radio frequency waveforms. In one embodiment, the control device 502 is further configured to calculate a set of weights such that the magnitude of the magnetic field equals that of a desired magnetic field within the region of interest. In one embodiment, the control device 502 is further configured to calculate a set of weights such that the magnitude of the electric field equals that of a desired electric field within the region of interest. In one embodiment, the control device 502 is further configured to generate localized heating pattern based on the electric field.

In one embodiment, the control device 502 is further configured to generate localized heating pattern based on the electric field, wherein the radio frequency energy also generates a magnetic field excitation pattern that can be observed in the image. In one embodiment, the control device 502 is further configured to compare the spatially localized heating pattern with the radio frequency excitation pattern in the image. In one embodiment, the control device 502 is further configured to calculate an electric field generated by the plurality of coils 503 based on the set of weights, and control to generate the localized heating based on the electric field. In one embodiment, the control device 502 is further configured to calculate an electric field generated by the plurality of coils 503 based on the set of weights, and control to generate the corresponding desired electric field excitation pattern that is determined from optimizing the magnetic field excitation pattern.

Taking into account that detailed description of the above operations have been described above with reference to FIGS. 1-4, the detailed description thereof will not be provided herein.

Figure 6:
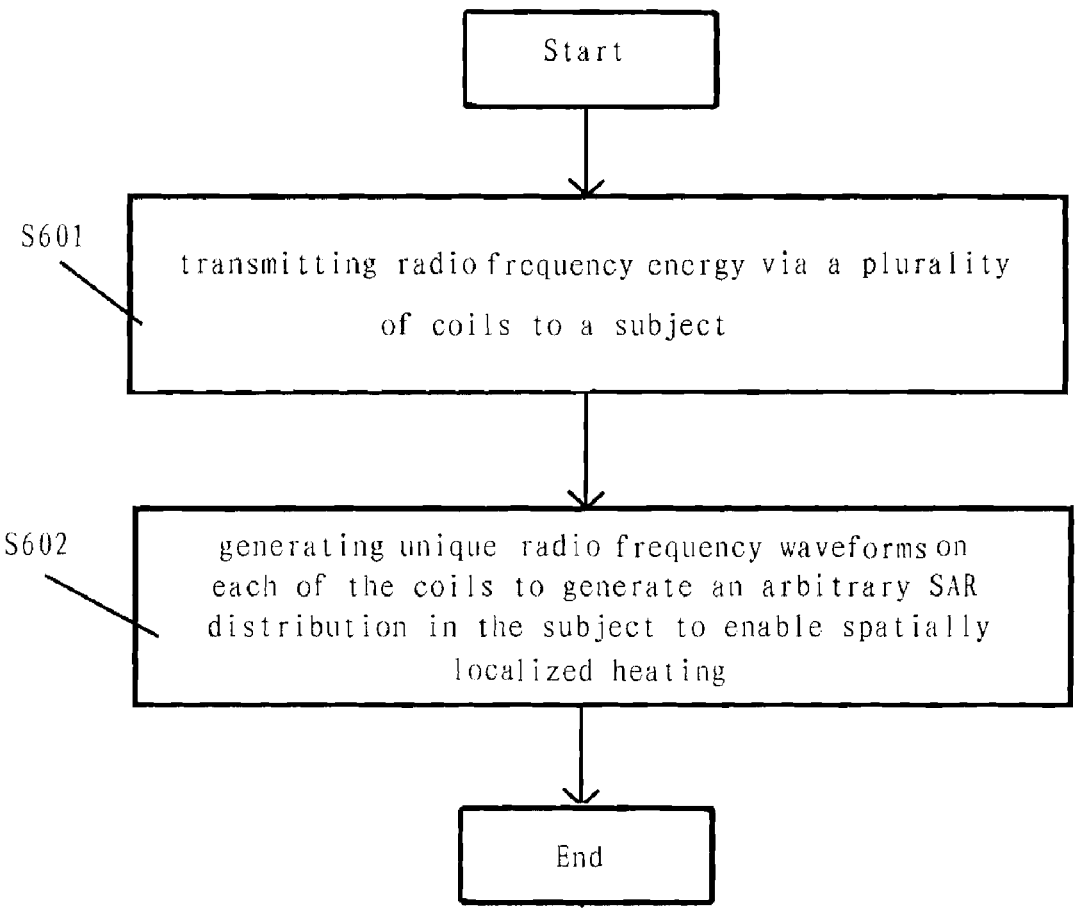
FIG. 6 is a flow chart of a method in accordance with one embodiment of the invention.

FIG. 6 is a flow chart of a method in accordance with a further embodiment of the invention. As shown in FIG. 6, in step 601, radio frequency energy is transmitted via a plurality of coils 503 to a subject 504, then in step 602, unique radio frequency waveforms are generated for each of the coils 503 to generate an arbitrary specific absorption rate (SAR) distribution in the subject 504 to enable spatially localized heating. Calibration of the $B_1$-field distribution of each coil element in 503 is implicit in the preceding discussion.

In the above embodiment, the plurality of coils 503 used to transmit radio frequency energy with unique radio frequency waveforms for each of the coils or unique magnitude and phase weights for each coil to generate an arbitrary specific absorption rate distribution in the subject 504 to enable spatially localized heating is also used to generate a magnetic resonance image.

In the above embodiment, the plurality of coils 503 used to transmit radio frequency energy with unique radio frequency waveforms for each of the coils or unique magnitude and phase weights that generate a spatially localized heating pattern also generates a unique radio frequency excitation pattern in the image.

In the above embodiment, the plurality of coils 503 used to transmit radio frequency energy with unique radio frequency waveforms for each of the coils or unique magnitude and phase weights that generate a spatially localized heating pattern can be array around the subject 504 in any appropriate pattern that permits full coverage of all regions of interest within the subject 504.

Taking into account that detailed description of the above operations have been described above with reference to FIGS. 1-4, the detailed description thereof will not be provided herein.

Figure 7:
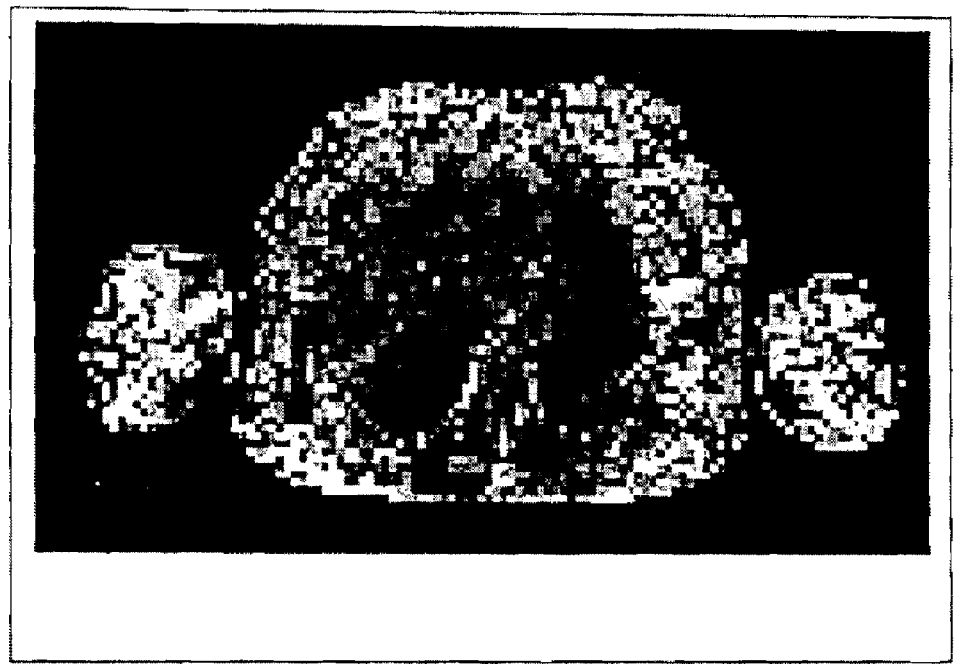
FIG. 7 shows the specific absorption rate (SAR) pattern by using a conventional sinusoidal distribution of current in a quadrature body coil.
Figure 8:
FIG. 8 shows SAR pattern by using an 8-channel parallel coil and a choice of coil weights $\{w_m^e\}$.

FIG. 7 shows the SAR pattern by using a conventional sinusoidal distribution of current in a quadrature body coil. FIG. 8 shows the SAR pattern by using an 8-channel parallel transmit coil and a choice of coil weights, $\{w_m^e\}$. The SAR pattern in FIG. 8 is noticeably altered to favor greater power deposition (and heating) in the anterior right side of the body. These results demonstrate a proof-of-concept of the method for adjusting or localizing the heating pattern within the body by using multiple coils.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for generating a localized heating, comprising:
    transmitting a spatially localized or shaped electromagnetic field via a plurality of coils to a subject and generating magnetic resonance signals;
    performing magnetic resonance imaging based on the magnetic resonance signals to generate an image of a region of interest of the subject; and
    controlling the plurality of coils to radiate radio frequency (rf) energy to generate the localized heating in the region of interest.

2. A method recited in claim 1, further comprising a step of generating unique radio frequency (rf) waveforms in each of the plurality of coils or adjusting the amplitude and phase of the unique radio frequency waveforms to generate the localized heating.

3. A method recited in claim 1, further comprising a step of calculating a set of weights such that the magnitude of a magnetic field of the electromagnetic field equals that of a desired magnetic field within the region of interest.

4. A method recited in claim 3, further comprising a step of generating localized heating pattern based on the electromagnetic field, wherein the radio frequency energy also generates a magnetic field excitation pattern that can be observed in the image.

5. A method recited in claim 4, further comprising a step of predicting the spatially localized heating pattern by comparing the radio frequency magnetic field excitation pattern in the image with a desired magnetic field excitation pattern.

6. A method recited in claim 4, further comprising a step of predicting the spatially localized heating pattern by inferring the corresponding radio frequency electric field distribution by the measured radio frequency magnetic field excitation pattern in the image.

7. A method recited in claim 3, wherein the magnetic field is given as:

$$b_n = \sum_{m=1}^{\#coils} B_{n,m} * w_m$$

wherein $B_{n,m}$ is the magnetic field generated at location n by coil m when the coil alone is driven by a radio frequency waveform, and $w_m$ is a complex weight capturing the amplitude and phase control of the radio frequency waveform that drives the mth coil, and represents the weight for the mth coil in generating the magnetic field at discrete points n.

8. A method recited in claim 7, wherein the set of weights are calculated based on the following equation:

$$|b_n' - b_n|^2 \to 0$$

wherein $b_n$ is the magnetic field generated by the plurality of coils, while $b_n'$ is the desired magnetic field.

9. A method recited in claim 3, further comprising a step of calculating an electric field generated by the plurality of coils based on the set of weights, and generating the localized heating based on the applied electromagnetic field with the set of weights.

10. A method recited in claim 9, wherein the electric field is given as:

$$e_n = \sum_{m=1}^{\#coils} E_{n,m} * w_m$$

where $E_{n,m}$ is the electric field generated at location n by coil m when the coil alone is driven by a radio frequency waveform, and $w_m$ is a complex scalar capturing the amplitude and phase control of the radio frequency waveform that drives the mth coil, and represents the weight for the mth coil in generating the electric field at discrete points n.

11. A method recited in claim 10, wherein the electric field is calculated based on the following equation:

$$|e_n'|^2 - |e_n|^2 \to 0$$

where $e_n$ is the electric field generated by the plurality of coils, $e_n'$ is the desired electric field distribution, and $|e_n'|^2$ is maximum in the region of interest and minimum outside the region of interest.

12. A method recited in claim 9, wherein the electric field and magnetic field are related by the following equation:

$$\vec{E} = (\mu(\sigma - j\omega\in))^{-1} \nabla \times \vec{B}$$

where $\mu$ is the magnetic permeability, $\sigma$ is the conductivity, $\in$ is the dielectric constant, $\omega$ is the resonant frequency, and $j = (-1)^{1/2}$.

13. A method recited in claim 12, wherein the electric field is predicted from the magnetic field excitation pattern in the image using an approximation of the z-component of the magnetic ($B_1$) field.

14. A method recited in claim 13, wherein the approximation of the z-component of the magnetic ($B_1$) field is constrained to a subset of allowable solutions by the boundary values set by an imaging experiment.

15. A method recited in claim 1, further comprising a step of calculating a set of weights such that the magnitude of an electric field of the electromagnetic field equals that of a desired electric field within the region of interest.

16. A method recited in claim 1, wherein the magnetic resonance imaging and the localized heating are performed simultaneously or in an interleaved fashion.

17. A method for generating a localized heating, comprising:
   transmitting radio frequency energy via a plurality of coils to a subject; and
   generating unique radio frequency waveforms on each of the coils to generate an arbitrary specific absorption rate distribution in the subject to enable spatially localized heating.

18. A method recited in claim 17, wherein the plurality of coils used to transmit radio frequency energy with unique radio frequency waveforms for each of the coils or unique magnitude and phase weights for each coil to generate an arbitrary specific absorption rate distribution in the subject to enable spatially localized heating is also used to generate a magnetic resonance image.

19. A method recited in claim 17, wherein the plurality of coils used to transmit radio frequency energy with unique radio frequency waveforms for each of the coils or unique magnitude and phase weights that generate a spatially localized heating pattern also generates a unique radio frequency excitation pattern in the image.

* * * * *